(12) United States Patent
Hoffmann et al.

(10) Patent No.: US 7,771,708 B2
(45) Date of Patent: *Aug. 10, 2010

(54) ANTI-FAT COMPOSITION FOR HAIR AND SCALP

(75) Inventors: Martin Hoffmann, Zwingenberg (DE); Bettina Schupp, Bickenbach (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 1410 days.

This patent is subject to a terminal disclaimer.

(21) Appl. No.: 11/113,675

(22) Filed: Apr. 25, 2005

(65) Prior Publication Data

US 2005/0244361 A1 Nov. 3, 2005

(30) Foreign Application Priority Data

Apr. 30, 2004 (EP) .................................. 04010245

(51) Int. Cl.
*A61Q 5/00* (2006.01)
(52) U.S. Cl. .................................. 424/70.11; 424/70.1
(58) Field of Classification Search .................. None
See application file for complete search history.

(56) References Cited

U.S. PATENT DOCUMENTS

| | | | | | |
|---|---|---|---|---|---|
| 3,950,532 | A | * | 4/1976 | Bouillon et al. | 514/445 |
| 4,381,259 | A | * | 4/1983 | Homma et al. | 510/122 |
| 4,985,452 | A | * | 1/1991 | Brandes et al. | 514/383 |
| 2003/0129268 | A1 | * | 7/2003 | Msika et al. | 424/776 |

* cited by examiner

*Primary Examiner*—Eric E. Silverman
(74) *Attorney, Agent, or Firm*—Norris, McLaughlin & Marcus

(57) ABSTRACT

This invention is about anti-fat cleansing composition for hair and scalp with an active ingredient derived from natural sources. Active ingredient used is butyl esters of fatty acids of avocado oil, which is known as 5-α-Avocuta.

7 Claims, No Drawings

ANTI-FAT COMPOSITION FOR HAIR AND SCALP

This invention is about anti-fat cleansing composition for hair and scalp with an active ingredient derived from natural source. Active ingredient used is butyl esters of fatty acids of avocado oil, which is known as 5-α-Avocuta.

Hair care compositions have been found their application for many decades. Although the state of the art is quite well established there is still need for improvements.

Greasiness of hair and scalp is one of the main problems reflected in the surveys carried out in hair care field. Consumers are often having problem with quick greasiness of their scalp and, therefore, hair, as this leads them to wash their hair more frequently.

Attempts have been made to offer products to solve this problem. Products available on the market have not been found to be satisfactory in solving above mentioned problem. Therefore, needs are there to offer new technologies in the field of hair and scalp care.

Natural ingredients as well ingredients derived from natural resources have always been attractive to the consumer. Compositions containing natural ingredients especially derived from the edible ones have always been regarded as safer than any other composition offered mainly based on synthetic raw materials. Designing modern cosmetic formulations solely on the basis of natural ingredients will probably take more time in the future.

Zinc salts such as Zinc salt of pyrrolidoncarboxylic acid (PCA) has been used for its anti-fat effect in hair and scalp cleansing and/or scalp care products. The effect obtained with this ingredient has not been found satisfactory and new developments with improved performance are therefore desirable.

Thus, the objective of the present invention is finding out compositions suitable for hair and scalp cleansing and showing satisfactory or improved anti-fat effect. It has surprisingly been found out that by incorporating butyl esters of fatty acids of avocado oil, which is known as 5-α-Avocuta, satisfactory anti-fat effect is observed. The anti fat effect of the compositions is determined by a use test with end users, admitting having greasy hair and scalp and using normally anti-fat hair and scalp cleansing products claiming the anti-fat effect.

Butyl esters of fatty acids of avocado oil is prepared from natural avocado oil by first obtaining fatty acids and esterifying. Main fatty acid component in 5-α-Avocuta is oleic acid. It comprises furthermore palmitic, palmitoleic and linoleic acids. It comprises mainly unsaturated fatty acids.

Hair and scalp cleansing composition of the present invention comprises butyl esters of fatty acids of avocado oil (5-α-Avocuta) at a concentration of 0.01 to 4%, preferably 0.01 to 2%, more preferably 0.01 to 1% by weight calculated to total composition.

Hair and scalp cleansing composition of the present invention is shampoo composition which can be in the form of a thickened liquid, independent from its appearance either transparent or semi-transparent or pearly non-transparent, packed in a bottle, or in the form of a thin liquid packed either in a bottle equipped with a pump which delivers the content in the form of foam or packed in a pressurized container, comprising at least one cosmetically acceptable gas, which delivers its content as well in the form of foam. It should as well be noted that with the term thickened liquid compositions, gel type cleansing compositions are as well covered independent from their appearance.

Hair and scalp cleansing composition of the present invention comprises at least one surfactant selected from anionic, non-ionic and/or amphoteric or zwitterionic surfactants at a concentration range of 2 to 60%, preferably 5 to 50% and more preferably 5 to 40% by weight, calculated to the total composition. It is the preferred embodiment of the present invention that hair and scalp cleansing composition comprises at least one anionic surfactant.

Anionic surfactants suitable within the scope of the invention are preferably present in an amount from 1 to about 30%, preferably 2 to 25% and most preferably 2-20% by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

$$R_1—(C_2H_4O)_n—O—CH_2COOX,$$

wherein $R_1$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

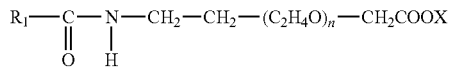

wherein $R_1$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof. It is also possible to use mixtures of several anionic surfactants, for example, a mixture of an α-olefin sulfonate and a sulfosuccinate, preferably in a proportion of 1:3 to 3:1, or of an ether sulfate and a polyether carboxylic acid or alkyl amidoether carboxylic acid.

An overview of the anionic surfactants used in liquid body cleansing compositions can furthermore be found in the monography of K. Schrader, "Grundlagen und Rezepturen der Kosmetika", $2^{nd}$ Ed.(1989, Hüthig Buchverlag), pp. 595-600 and pp. 683 to 691.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the hair and scalp cleansing composition according to the present invention are nonionic surfactants, preferably in admixture with anionic surfactants.

These are described in Schrader, I.c., on pages 600-601 and pp. 694-695. Especially suited are alkyl polyglucosides of the general formula

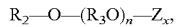

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides in an amount from about 0.25% to about 5%, preferably about 0.5% to about 3.5% by weight, calculated to the total composition.

Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the compositions according to the invention can also contain amphoteric or zwitterionic surfactants, for example in an amount from about 0.5% to about 10%, preferably from about 1% to about 7.5% by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

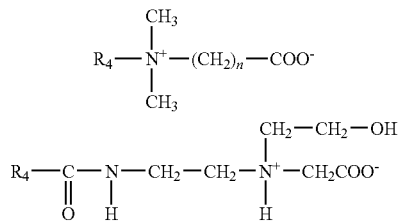

wherein $R_4$ is a $C_8$-$C_{18}$-alkyl group and n is 1 to 3; sulfobetaines of the structure

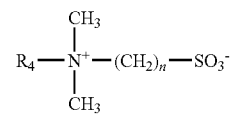

wherein $R_4$ and n are same as above;
and amidoalkyl betaines of the structure

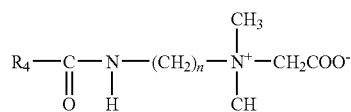

wherein $R_4$ and n are same as above.

Hair and scalp cleansing composition of the present invention comprises cationic hair conditioning agents. Cationic conditioning agents are selected from cationic amphiphilic compounds, cationic polymers and cationic silicone derivatives. The compositions can as well comprise other conditioning agents such as oily substances and non-ionic substances.

Cationic surfactants as conditioning agents according to the present invention are represented with the general formula below:

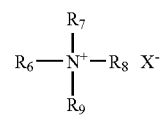

where $R_6$ is a saturated or unsaturated, branched or non-branched alkyl chain with 8-22 C atoms or

where $R_{10}$ is saturated or unsaturated, branched or non-branched alkyl chain with 7-21 C atoms and n has typical value of 0-4 or

where $R_{11}$ is saturated or unsaturated, branched or non-branched alkyl chain with 7-21 C atoms and n has typical value of 0-4, and $R_7$ is a hydrogen, lower alkyl chain with 1 to 4 carbon atoms, saturated or unsaturated, branched or non-branched alkyl chain with 8-22 C atoms or

where $R_{10}$ is saturated or unsaturated, branched or non-branched alkyl chain with 7-21 C atoms and n has typical value of 0-4 or

where $R_{11}$ is saturated or unsaturated, branched or non-branched alkyl chain with 7-21 C atoms and n has typical value of 0-4, and $R_8$ and $R_9$ are independent from each other H or lower alkyl chain with 1 to 4 carbon atoms, and X is chloride, bromide or methosulfate.

Suitable cationic amphiphilic compounds as conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate.

From the above quaternary ammonium compounds disclosed with the general formula, especially preferred are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially preferred are these compounds are known per se and on the market, for example, under the trade name "INCROQUAT® HO" or "OCS". Those compounds are known with a general ingredient category under "amidoquat" in the cosmetic industry.

Composition of the present invention comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The cationic polymers also include the quaternized products of graft polymers from organopolysiloxanes and polyethyl oxazolines described in EP-A 524 612 and EP-A 640 643.

Cationic conditioning agents are used alone or in combination with each other. As a result, a composition failing in the scope of the present invention can contain for example single cationic polymer or single cationic surfactant or single cationic silicone derivative as the sole conditioner as well can contain cationic polymer, cationic surfactant and cationic silicone derivative in the same composition as conditioning compounds.

Typical concentration range for cationic conditioners mentioned above can be 0.01-7.5% by weight, preferably 0.05-5% by weight, more preferably 0.1-2.5% by weight calculated to the total composition.

Oily substances as conditioners according to the present invention are selected from silicone oils either volatile or non-volatile, natural and synthetic oils. Among silicone oils those can be added to the compositions include dimethicone, dimethiconol, polydimethylsiloxane, DC fluid ranges from Dow Corning.

Natural oils suitable are such as olive oil, almond oil, avocado oil, weizenkeim oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof, as well as mineral oils such as paraffin oil and petrolatum.

Lipophilic compounds such as fatty acid esters are as well suitable for the composition of the present invention. Those are such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glyceryl cocoate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula,

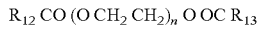

where $R_{12}$ and $R_{13}$ are independent from each other saturated, unsaturated or branched or non-branched alkyl chain with 7 to 21 C atoms and n is typically 2-100.

Typical concentration range for any of the additional conditioners mentioned above other than cationic conditioning compounds can be 0.01-15% by weight, preferably 0.05-5% by weight calculated to the total composition.

The compositions according to the invention can also comprise further agents, such as protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed.

Among the natural ingredients in the form of an extract, especially preferred component of the composition according to the invention is green tea extract. This tea extract is obtained from the leaves, leaf buds and tender stems of the tea shrub, *Camellia sinensis* or *Camellia oleifera*, by aqueous or hydro-alcoholic extraction and subsequent spray-drying. In difference to black tea, green tea is a non-fermented product obtained from the *Thea sinensis* or *Thea assamica* species. An overview of the biological and pharmacological effects of green tea and the ingredients thereof can be found, e.g., in an article by A. Pistorius, "Seifen-Öle-Fette-Wachse-Journal", Volume 122., No. 7/1996, pages 468 to 471, to which reference is made. The content of green tea extract is variable in the compositions according to the invention. It preferably ranges from 0.01% to 10%, preferably 0.05% to 5% by weight, calculated to the total composition and the pulverulent extract.

Hair and scalp cleansing composition of the present invention can have transparent appearance as well as a pearly appearance. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in shampoo compositions in crystalline form, i.e. so called pearl-shine agents. The preferred once are PEG-3 distearate and ethylene glycol distearate. The concentration of those can typically be from 0.1 to 3%, preferably 0.5 to 2% by weight, calculated to the total composition.

Solubilizers may be added to the compositions especially when oily substances are chosen as conditioning agents and fragrance oils with highly lipophilic properties. Typical solubilizers may be hydrogenated castor oil known with the trade mark Cremophor RH series from BASF. It should be noted that as well the surfactant mixture can be a good solubilizer for fragrance oils. Typical concentration of the solubilizers can be in the range of 0.01-2% by weight, preferably 0.1-1% by weight, calculated to the total composition. It should be noted without limiting their use that the solubilizers are especially used in the clear cleansing and/or conditioning preparations in order to overcome the turbidity caused by addition of lipophilic materials.

Needs of hair and scalp can certainly not be limited to a single problem. Therefore it is often needed multipurpose products such as and anti fat hair and scalp cleansing composition with UV filter for protection hair and scalp from damaging effects of UV rays as well with an antidandruff ingredient for solving problems of greasy hair and scalp and with dandruff.

Compositions of the present invention can comprise UV filters either for stabilization of the product colour or for protection of hair from environmental influences such as loss of elasticity, loss of hair colour (bleaching effect of sun light). The UV-absorbing substance is preferably selected from the following compounds:

4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-di hydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher. The preferred amount of the UV-absorber ranges from about 0.01% to 2.5%, more preferably from 0.05% to 1% by weight, calculated to the total composition.

Antidandruff agents such as piroctone olamine (Octopirox), zinc pyrrithion, climbazol can as well be used when an antidandruff effects is targeted. Typical useful concentration range for antidandruff agents is between 0.1-2% by weight calculated to the total composition.

The pH of the hair and scalp cleansing compositions according to the present invention is in the range of 3 to 8, preferably 3 to 7, more preferably 4 to 7. For adjusting the pH of the said compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be chosen in a way that composition reaches the desired pH value as given above. Typically concentration for acids can be 0.01-3% by weight, preferably 0.05-2% by weight, more preferably 0.05-1.5% by weight calculated to the total composition. The pH of the composition can also be adjusted to the required pH by using alkaline solution such as sodium hydroxide, potassium hydroxide or their salts with those acids mentioned above in the case that at the selected acid concentration pH of the composition is lower than that of the aimed value.

The viscosity of the compositions in the form of a conventional shampoo can have the viscosity in the range of between about 1000 and about 10,000 mPa.s at 20° C., measured according to Brookfield or Höppler at a shear rate of 10 sec$^{-1}$.

Whereas hair and scalp cleansing compositions dispensed form an aerosol and/or pump foamer should preferably be very liquid, i.e. viscosity values more than approximately 200 mPa.s measured as given above are not appropriate.

Furthermore, hair and scalp cleansing compositions of the present invention can comprise all substances customarily found in such preparations.

Examples of such substances are complexing agents, dyestuffs, preservatives, pH-regulants, viscosity regulants such as inorganic salts or polymers to the extent they are not already contained in the initial surfactant mixtures, fragrances, pearl-gloss agents, thickening agents, moisturizers, etc. Furthermore, compositions dispensed from an aerosol preferably do not contain any preservative.

The following examples illustrate the invention.

EXAMPLE 1

| Hair and Scalp Cleansing Composition | |
| --- | --- |
| Sodium lauryl ether sulfate (~2.5EO) | 10.0 (% by wt.) |
| $C_{12}$–$C_{14}$-alkyl polyglucoside (P.D.: ~1.5) | 3.0 |
| Cocoamidopropyl betaine | 4.0 |
| 5-α-Avocuta | 0.3 |
| Polyquaternium-10 | 0.4 |
| PEG-55-1.2-propyleneglycol oleate | 1.0 |
| Panthenol | 0.3 |
| Sodium chloride | q.s 5.000 mPa · s* |
| Preservative, fragrance | q.s |
| Citric acid | q.s pH 5.0 |
| Water | ad 100.0 |

*measured as given in the description.

Shampoo composition is prepared by combining first the surfactants and subsequently other ingredients are added to the surfactant mixture except that polymer is first dissolved in water before adding to the surfactant mixture.

The shampoo according to the invention developed a full, creamy lather and provided the hair with good wet and dry combability, volume, full and soft body as well as gloss and elasticity.

The composition is tested for demonstrating its anti fat effect in a use test with 10 end users admitting having greasy hair and using normally anti-fat hair and scalp cleansing products claiming the anti-fat effect. In a control group quantitatively the same compositions as above but not containing 5-α-Avocuta is tested in the same way. All participants, male, aging 20 to 45, 10 in each group, are asked to use the hair and scalp cleasing composition for the period of 3 weeks. Prior to the test period their washing habits are evaluated. Avarage hair and scalp washing frequency is 6 in a week.

After 3 week of usage, average wash frequency in the group using the composition according to the example 1 was dropped to 3 in a week on average (most of the test persons answered the question as every other day) whereas in the group using the composition not comprising 5-α-Avocuta (non-inventive composition) did not change at all, the average number was 6 (most of the test persons answered the question as every day). In the group using the inventive composition, preference was approximately 90% towards the inventive composition when compared to shampoos used normally. In the group using non-inventive composition, this was only 30%.

The above results clearly show the anti-fat effect of the hair and scalp cleansing composition according to the present invention.

Similar results are observed with the following compositions.

EXAMPLE 2

| Hair and Scalp Cleansing Composition | |
| --- | --- |
| Sodium alkyl ether sulfate (~2.5EO) | 6.5 (% by wt.) |
| $C_{12}$–$C_{14}$-Alkyl polyglucoside (P.D.: ~1.5) | 2.9 |
| Cocoamidopropyl betaine | 1.8 |
| Lauryl hydroxy sultaine | 1.0 |
| Sodium lauroyl glutamate | 1.1 |
| PEG-35-1,2-propyleneglycol cocoate | 2.0 |
| PEG-3-distearate | 0.6 |
| 5-α-Avocuta | 0.2 |
| Triglycerol | 0.2 |
| Cationic wheat protein hydrolyzate | 0.3 |
| Polyquaternium-6 | 0.3 |
| Aloe extract | 0.1 |
| Perfume, preservative | q.s |
| Sodium chloride | q.s 3.000 mPa · s* |
| Citric acid | q.s pH 6.0 |
| Water | to 100.0 |

*measured as given in the description.

EXAMPLE 3

| Shampoo | |
| --- | --- |
| Sodium lauryl ether sulfate (~2 EO) | 10.5 (% by wt.) |
| $C_{12}$–$C_{14}$-Alkyl polyglucoside | 2.5 |
| Polyoxyethylene-(55)-1.2-propanediol dioleate | 2.0 |
| Polyquaternium-10 | 0.3 |
| 5-α-Avocuta | 0.5 |
| Isopropyl myristate | 0.5 |
| PEG-3-distearate | 0.8 |
| Thyme extract | 0.5 |
| Citric acid | q.s. pH 4.5 |
| Glycerol | 1.0 |
| Perfume, Preservative | q.s |
| Sodium chloride | q.s 6.000 mPa · s* |
| Water | ad 100.0 |

*measured as given in the description.

EXAMPLE 4

| Anti-fat and Anti-Dandruff Shampoo Composition | |
| --- | --- |
| Sodium lauryl ether sulfate (~2.5EO) | 8.0 (% by wt.) |
| Disodium lauryl ether sulfosuccinate | 1.0 |
| $C_{12}$–$C_{14}$-Alkyl polyglucoside (P.D.: ~1.5) | 2.5 |
| Cocoamidopropyl betaine | 2.0 |
| Polyquaternium-11 | 0.4 |
| Wheat protein hydrolyzate | 0.5 |
| 5-α-Avocuta | 0.5 |
| Panthenol | 0.3 |
| Piroctone olamine | 0.4 |
| Citric acid | q.s. to pH 5.5 |
| Perfume, Preservative | q.s |
| Sodium chloride | q.s to 3500 mPa · s* |
| Water | ad 100.0 |

*measured as given in the description.

In addition to outstanding anti-fat effect, anti-dandruff effect is as well evaluated to be excellent.

EXAMPLE 4

| Anti-fat Shampoo Composition - Aeresol | |
| --- | --- |
| Sodium lauryl ether sulfate (~2.5EO) | 10.0 (% by wt.) |
| Cocoamphodiacetate | 1.5 |
| $C_{12}$–$C_{14}$-Alkyl polyglucoside (P.D.: ~1.5) | 2.0 |
| Polyquaternium-11 | 0.3 |
| PEG-7-Glyceryl cocoate | 0.7 |
| 5-α-Avocuta | 0.3 |
| Citric acid | q.s. to pH 5.5 |
| Perfume | q.s |
| Water | ad 100.0 |

The above composition is filled into aerosol cans with 5% customary Propane/butane propellant mixture. The product so obtained showed excellent foam and distribution properties. The observed anti-fat effect was similar to the example 1.

The same composition was as well used as confectioned in a pump-foamer device. Similar effects were observed.

The invention claimed is:

1. Hair and scalp cleansing composition comprising at least one cleansing surfactant selected from anionic, non-ionic and amphoteric surfactants, a hair conditioning agent comprising a cationic polymer, and butyl esters of fatty acids of avocado oil, wherein the hair conditioning agent is an amphiphilic cationic compound according to the formula

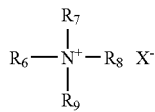

where $R_6$ is a saturated or unsaturated, branched or non-branched alkyl chain with 8-22 C atoms or $R_{10}$ CO NH $(CH_2)_n$ where $R_{10}$ is saturated or unsaturated, branched or non-branched alkyl chain with 7-21 C atoms and n is 1-4 or $R_{11}$ CO O $(CH_2)_n$ where $R_{11}$ is saturated or unsaturated, branched or non-branched alkyl chain with 7-21 C atoms and n is 1-4, and $R_7$ is a hydrogen, lower alkyl chain with 1 to 4 carbon atoms, saturated or unsaturated, branched or non-branched alkyl chain with 8-22 C atoms or $R_{10}$ CO NH $(CH_2)_n$ where $R_{10}$ is saturated or unsaturated, branched or non-branched alkyl chain with 7-21 C atoms and n is 1-4 or $R_{11}$ CO O $(CH_2)_n$ where $R_{11}$ is saturated or unsaturated, branched or non-branched alkyl chain with 7-21 C atoms and n is 1-4, and $R_8$ and $R_9$ are independent from each other H or lower alkyl chain with 1 to 4 carbon atoms, and X is chloride, bromide or methosulfate.

2. Hair and scalp cleansing composition according to claim 1 wherein the surfactant is anionic surfactant.

3. Hair and scalp cleansing composition according to claim 1 wherein the surfactant is non-ionic surfactant.

4. Hair and scalp cleansing composition according to claim 1 wherein the surfactant is amphoteric surfactant.

5. Hair and scalp cleansing composition according to claim 1, comprising butyl esters of fatty acids of avocado oil at a concentration of 0.01 to 4% by weight of the total composition.

6. Hair and scalp cleansing composition according to claim 1, comprising one or more surfactants at a concentration of 2 to 60% by weight of the total composition.

7. Method of reducing greasiness of hair and scalp comprising administering to the hair and scalp an effective amount of the composition of claim 1.

* * * * *